(12) United States Patent
Lundgreen et al.

(10) Patent No.: US 8,881,580 B2
(45) Date of Patent: Nov. 11, 2014

(54) PROCESS ANALYSIS UNIT

(75) Inventors: Ulrich Lundgreen, Guetersioh (DE); Aria Farjam, Duesseldorf (DE)

(73) Assignee: Hach Lange GmbH, Berlin (DE)

( * ) Notice: Subject to any disclaimer, the term of this patent is extended or adjusted under 35 U.S.C. 154(b) by 164 days.

(21) Appl. No.: 13/392,098

(22) PCT Filed: Jul. 28, 2010

(86) PCT No.: PCT/EP2010/060947
§ 371 (c)(1),
(2), (4) Date: Apr. 20, 2012

(87) PCT Pub. No.: WO2011/035959
PCT Pub. Date: Mar. 31, 2011

(65) Prior Publication Data
US 2012/0198921 A1    Aug. 9, 2012

(30) Foreign Application Priority Data
Aug. 25, 2009  (EP) ..................................... 09168536
Apr. 1, 2010   (WO) ................. PCT/EP2010/054402

(51) Int. Cl.
*G01N 33/00* (2006.01)
*G01N 21/11* (2006.01)
(Continued)

(52) U.S. Cl.
CPC ............ *G01N 21/8507* (2013.01); *G01N 21/11* (2013.01); *B01L 2200/10* (2013.01);
(Continued)

(58) Field of Classification Search
CPC .................. F04B 43/1253; A61B 2560/0443; A61B 5/202; A61B 5/205; A61B 1/32

USPC .......................................... 73/61.41; 356/436
See application file for complete search history.

(56) References Cited

U.S. PATENT DOCUMENTS 4,583,920 A    4/1986  Lindner
5,411,889 A *  5/1995  Hoots et al. ........................ 436/6
(Continued)

FOREIGN PATENT DOCUMENTS

DE    26 39 992 A1    3/1978
DE    101 26 054 A1   6/2002
(Continued)

OTHER PUBLICATIONS

Wang et al.: "Automatic bio-sampling chips integrated with micro-pumps and micro-valves for disease detection", Biosendors and Bioelectronics, vol. 21, pp. 419-425 (2005).

(Continued)

*Primary Examiner* — Peter Macchiarolo
*Assistant Examiner* — Mohammed Keramet-Amircola
(74) *Attorney, Agent, or Firm* — Norman B. Thot (57) ABSTRACT

A process analysis unit includes a base module and an exchangeable cartridge module. The base module comprises at least one independent pump drive, and an analyte sensor without a fluidic measuring section. The cartridge module comprises a liquid reservoir tank, a sample taking device, at least one drive-less pump mechanism configured as a peristaltic membrane pump, a fluidic measuring section for the analyte sensor, and a plastic material plate with groove-like microfluidic channels configured to connect the liquid reservoir tank, the at least one drive-less pump mechanism, and a measuring section. The drive-less pump mechanism is driven pneumatically and pumps a liquid from the liquid reservoir tank. When the cartridge module is connected to the base module, the at least one drive-less pump mechanism is connected to and is driven by the at least one independent pump drive, and the fluidic measuring section is connected to the analyte sensor.

7 Claims, 6 Drawing Sheets

(51) Int. Cl.
*F04B 43/12* (2006.01)
*B01L 3/00* (2006.01)
*G01N 35/10* (2006.01)
*G01N 21/85* (2006.01)
*F04B 43/08* (2006.01)
*G01N 21/84* (2006.01)
*G01N 21/03* (2006.01)
*G01N 33/18* (2006.01)
*G01N 21/78* (2006.01)
*G01N 21/05* (2006.01)
*G01N 1/40* (2006.01)

(52) U.S. Cl.
CPC *G01N 2021/8411* (2013.01); *G01N 2021/0346* (2013.01); *G01N 2021/0325* (2013.01); *F04B 43/12* (2013.01); *B01L 2400/0481* (2013.01); *G01N 33/18* (2013.01); *G01N 21/78* (2013.01); *G01N 21/05* (2013.01); *B01L 3/50273* (2013.01); *G01N 2021/0321* (2013.01); *G01N 2001/4016* (2013.01); *G01N 35/1095* (2013.01); *G01N 2201/0218* (2013.01); *B01L 2300/0627* (2013.01); *F04B 43/082* (2013.01); *B01L 3/502715* (2013.01); *G01N 2201/024* (2013.01); *G01N 2021/054* (2013.01)
USPC .......................................................... 73/61.41

(56) References Cited

U.S. PATENT DOCUMENTS

| | | | |
|---|---|---|---|
| 5,593,290 A | 1/1997 | Greisch et al. | |
| 5,646,863 A | 7/1997 | Morton | |
| 5,695,719 A * | 12/1997 | Lynggaard et al. | 422/81 |
| 6,852,284 B1 * | 2/2005 | Holl et al. | 422/68.1 |
| 7,802,467 B2 * | 9/2010 | Wang | 73/61.41 |
| 7,817,276 B2 * | 10/2010 | Kiesel et al. | 356/436 |
| 2003/0194332 A1 * | 10/2003 | Jahn et al. | 417/395 |
| 2004/0013536 A1 | 1/2004 | Hower et al. | |
| 2004/0098211 A1 | 5/2004 | Binz et al. | |
| 2005/0214165 A1 * | 9/2005 | Babel et al. | 422/63 |
| 2008/0026373 A1 | 1/2008 | Rodinova | |
| 2008/0092638 A1 * | 4/2008 | Brenneman et al. | 73/61.41 |
| 2008/0245971 A1 * | 10/2008 | Wimberger-Friedl et al. | 250/458.1 |

FOREIGN PATENT DOCUMENTS

| | | | | |
|---|---|---|---|---|
| DE | 102 14 781 A1 | 10/2003 | | |
| DE | 102 27 032 A1 | 11/2003 | | |
| EP | 0 706 659 A1 | 4/1996 | | |
| EP | 1 353 069 A2 | 10/2003 | | |
| EP | 1 870 033 A1 | 12/2007 | | |
| EP | 1870033 A1 * | 12/2007 | | |
| EP | 2 163 892 A1 | 3/2010 | | |
| EP | 2163892 A1 * | 3/2010 | | G01N 21/85 |
| WO | WO 02/074043 A2 | 9/2002 | | |

OTHER PUBLICATIONS

Danfoss: "EVITA—In situ sensors for measuring ammonium, nitrate or orthophosphate", Danfoss Data Sheet (Aug. 1, 1997).

* cited by examiner

PROCESS ANALYSIS UNIT

CROSS REFERENCE TO PRIOR APPLICATIONS

This application is a U.S. National Phase application under 35 U.S.C. §371 of International Application No. PCT/EP2010/060947, filed on Jul. 28, 2010 and which claims benefit to European Patent Application No. 09168536.2, filed on Aug. 25, 2009 and to International Application No. PCT/EP2010/054402, filed Apr. 1, 2010. The International Application was published in German on Mar. 31, 2011 as WO 2011/035959 A1 under PCT Article 21(2).

FIELD

The present invention provides a process analysis unit as used, for example, in the field of water analysis in the form of an immersion probe, a tube insertion probe or a laboratory analysis apparatus.

BACKGROUND

Process analysis units perform quasi-continuous analyses for a quantitative determination of an analyte in water and, for that purpose, comprise one or a plurality of reservoir tanks to store liquids, such as carrier liquids, standard solutions and/or reagents needed in performing a water analysis. Pumps and liquid conduits are provided to transport the liquids in the analysis unit.

Upon depletion of a liquid supply in a reservoir tank, the respective reservoir tank must be refilled. In practical operation, problems are often caused, for example, by accumulations and crystallizations in the liquid conduits or in the liquid-carrying parts of the pumps. In addition to a regular refill or replacement of the reservoir tanks, these problems, as well as normal wear of wearing parts, for example, hoses or hose pumps, cause necessary maintenance work and repair, such as the cleaning and maintenance of pumps, replacement of hoses, etc.

SUMMARY

An aspect of the present invention is to provide a process analysis unit offering high operating reliability and requiring low maintenance effort.

In an embodiment, the present invention provides a process analysis unit for the determination of an analyte in water which includes a base module and an exchangeable cartridge module which is configured to be connected to the base module. The base module comprises at least one independent pump drive, and an analyte sensor without a fluidic measuring section. The base module does not comprise a liquid fluidic system. The cartridge module comprises the liquid fluidic system. The cartridge module comprises a liquid reservoir tank, a sample taking device, at least one drive-less pump mechanism configured as a peristaltic membrane pump, a fluidic measuring section for the analyte sensor, and a plastic material plate with groove-like microfluidic channels configured to connect the liquid reservoir tank, the at least one drive-less pump mechanism, and a measuring section. A section of the groove-like microfluidic channels is less than 5 mm². The drive-less pump mechanism is configured to be driven pneumatically and to pump a liquid from the liquid reservoir tank. The peristaltic membrane pump comprises pump chambers covered by a flexible liquid-tight pump membrane. When the cartridge module is connected to the base module, the at least one drive-less pump mechanism is connected to and is driven by the at least one independent pump drive, and the fluidic measuring section is connected to the analyte sensor. Each of a plurality of the at least one drive-less pump mechanism is associated with a respective at least one independent pump drive.

BRIEF DESCRIPTION OF THE DRAWINGS

The present invention is described in greater detail below on the basis of embodiments and of the drawings in which.

DETAILED DESCRIPTION

The process analysis unit of the present invention is of a modular structure and consists of a permanently used base module and an exchangeable cartridge module.

The base module comprises a pump drive motor and an analyte sensor without a liquid-carrying measuring section. The base module includes no fluidic system components, i.e., no liquid-carrying conduits, valves, measuring sections or pump mechanisms.

In contrast thereto, the cartridge module comprises at least one liquid reservoir tank, a drive-less pump mechanism for pumping the liquid from the reservoir tank, and a measuring section for the analyte sensor. The entire fluidic system is thus arranged in the cartridge module. The term pump mechanism refers to the fluidic transport mechanism, i.e., the part of the pump that is in direct contact with the liquid and effects transport within the fluidic system.

With the cartridge module inserted in the base module, the pump mechanism is driven by the pump drive via the coupling element, and the liquid-carrying measuring section is functionally associated to the analyte sensor such that the latter can perform measurements on analytes contained in the liquid.

Upon depletion of the liquid in the reservoir tank, such as the depletion of carrier liquid or reagent, the cartridge module with the entire fluidic system is exchanged. A replacement of the entire fluidic system thus occurs regularly or as a function of consumption. A separate maintenance or a wear-related repair of the fluidic system of the analysis unit is no longer necessary. This leads to a considerable reduction in maintenance effort. Due to the regular or consumption-based exchange of the entire fluidic system, troubles that could be caused by accumulations in the fluidic system or wear of fluidic system components, such as pump hoses, are reduced to a minimum.

In an embodiment, the pump mechanism can, for example, be designed as a peristaltic pump, and can, for example, be designed as a pneumatic peristaltic membrane pump. A peristaltic pump mechanism has a simple structure and may, for example, be formed by a flexible section of the liquid conduit continually deformed in the longitudinal direction by the coupling element.

The coupling element may be configured, for example, as three squeezing pistons arranged one behind the other in the longitudinal direction, which pistons successively squeeze the liquid conduit section in the longitudinal direction and in a liquid-tight manner, whereby they cause a peristaltic pumping movement. A pneumatic peristaltic pump is an embodiment in which, for example, the mechanical coupling is realized by applying overpressure or vacuum to a multi-stage membrane pump. The pump drive may thus be of an electromechanical or pneumatic design.

The inclusion of air in a liquid conduit is no problem for a peristaltic pump mechanism, since it is capable of suction against air. The use of a peristaltic pump mechanism also allows valves to be omitted, such as problem-prone check valves. The peristaltic pump mechanism offers the further possibility to pump a plurality of conduits at the same time, i.e. to pump a plurality of liquids at the same time, with only a single peristaltic pump mechanism. The peristaltic pump mechanism is a proven, economic and extremely reliable pumping technology.

In an embodiment of the present invention, the base module can, for example, comprise a plurality of independent pump drives associated to a plurality of independent pump mechanisms in the cartridge module. Basically, a plurality of pump mechanisms could be driven by a single pump drive. A dedicated pump drive can, for example, be associated in the base module to each pump mechanism in the cartridge module. In this manner, a plurality of liquid flows can be controlled independently.

In an embodiment of the present invention, the cartridge module can, for example, comprise a plurality of reservoir tanks. In the present instance, a reservoir tank is a tank for a reagent, a carrier liquid, a standard solution, a cleaning liquid or even for waste liquid. In this manner, an analysis unit can be provided with dialytic sample taking where no liquid escapes from the analysis unit while two cartridge modules are exchanged.

In an embodiment of the present invention, the analyte sensor can, for example, comprise, on the base module side, a photometer with an optical detector for a photometric determination of an analyte in a sample. The optical detector, or the photometer, determines the absorption, the fluorescence or the luminescence of an analyte in the sample contained in the measuring section of the fluidic system.

The sample may be taken from the water, for example, from waste water surrounding the analysis unit in a dialytic manner, for example. For this purpose, an embodiment of the cartridge module can, for example, comprise a dialysis membrane. In dialytic sampling, the water under analysis does not enter the analysis unit, but only molecules and ions migrate from the water into a carrier liquid beyond the dialysis membrane. The liquid volume within the analysis unit thus does not change substantially during the entire operating time between two cartridge module exchanges. The waste liquid can thus be collected in the analysis unit and will not get into the surrounding water.

In an embodiment of the present invention, the present analysis unit can, for example, be designed as a liquid-tight waste water immersion probe that is operated while being immersed directly in the water under analysis, such as waste water in a basin of a water treatment plant.

The cartridge module can, for example, comprise a plastic material plate which comprises the pump chambers of the pump mechanism and groove-like fluidic channels for connecting the reservoir tank, the pump mechanism and the measuring section. On the plastic material plate, a flexible and liquid-tight pump membrane is provided in the region of the pump chambers and a rigid cover is provided in the region of the channels for closing the channels.

In an embodiment of the present invention, the entire fluidic system can, for example, be of a microfluidic design so that the maximum channel section is, for example, 10 mm$^2$, or at most, for example, 5.0 mm$^2$. Only a fluidic system of microfluidic design allows providing an analysis unit that can work with the liquids in the reservoir tanks for a period that is sufficiently long under economic aspects.

Figure 1:
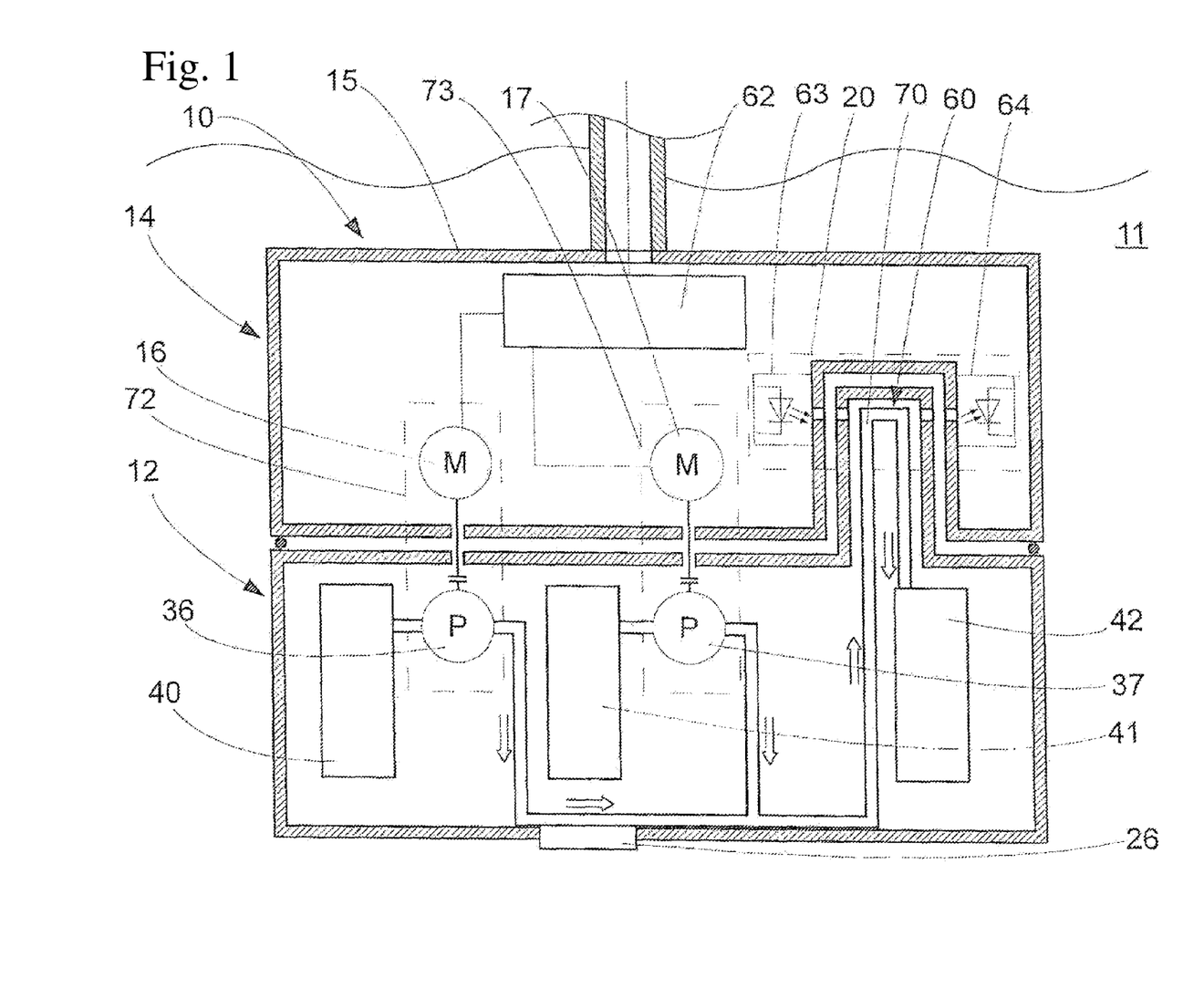
FIG. 1 shows a schematic illustration of an embodiment of an analysis unit in the form of an immersion probe.

FIG. 1 schematically illustrates a process analysis unit 10 designed as an immersion probe and serving for the analysis of water 11 in the interest of controlling a purification process. The analysis unit 10 is of bipartite and modular structure and is formed by a liquid-tight base module 14 and an exchangeable liquid-tight cartridge module 12. The base module 14 comprises a housing 15 into which the cartridge module 12 is inserted or which it is set to.

The base module 14 comprises an analyte sensor 20 in the form of a photometer, without a fluidic measuring section 60 which is provided in the cartridge module 12. On the base module side, the analyte sensor 20 comprises a light source 63 and an optical detector 64 in the form of a photodiode.

Figure 2:
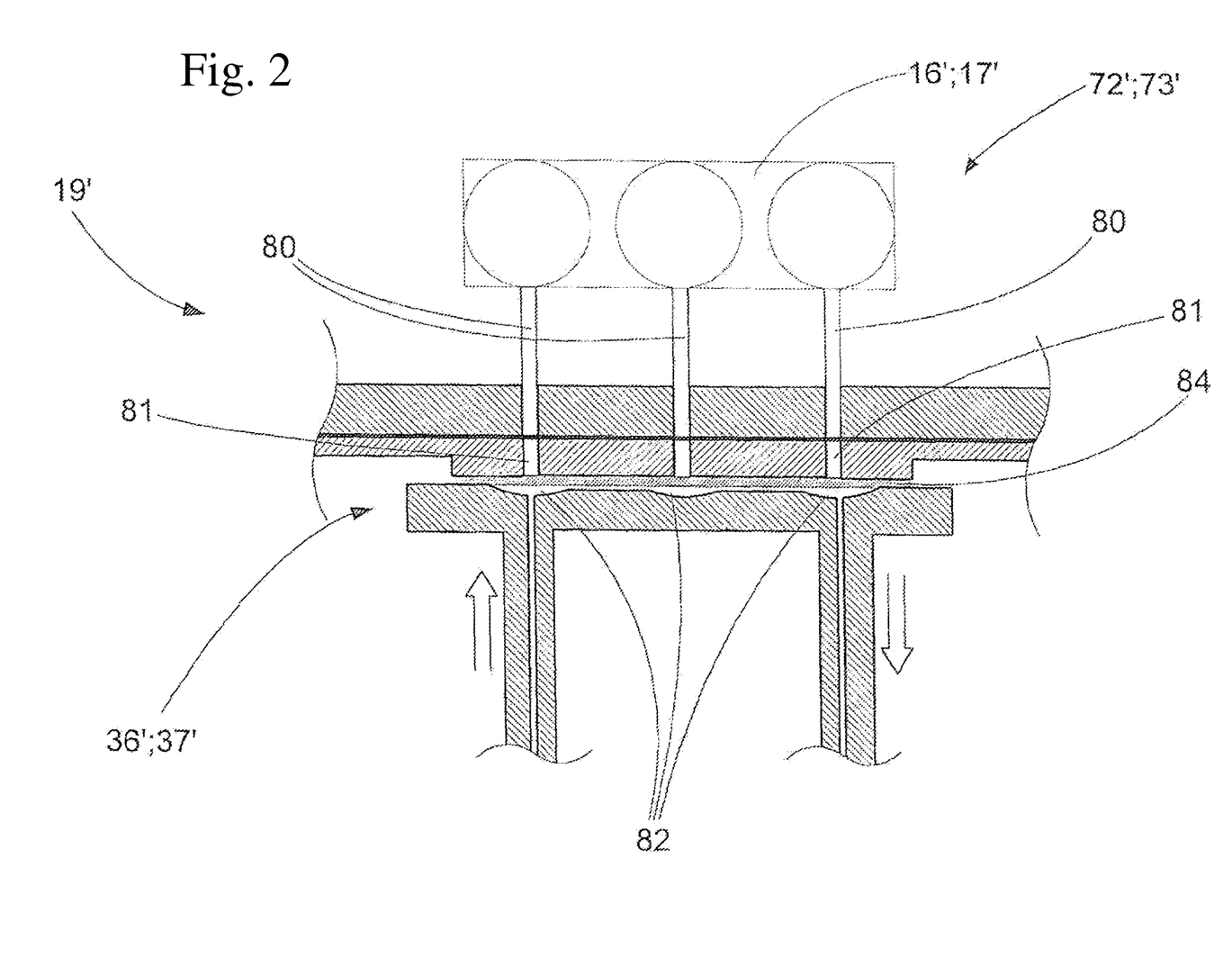
FIG. 2 shows an embodiment of a base-side pneumatic pump drive and a cartridge-side pump mechanism cooperating therewith.

As illustrated in FIG. 2, the pump of an embodiment may be of a pneumatic design, wherein the pump drive 16' is an air pump that successively applies overpressure or possibly also vacuum to three air channels 80 that are coupled with corresponding air channels 81 of the cartridge module 12. The air channels 81 of the cartridge module are closed by a pump membrane 84 beneath which three pump chambers 82 are formed.

If an overpressure is applied in the air channel 80 by the pump drive 16', the pump membrane 84 expands into the pump chamber 82 therebelow and displaces the liquid contained therein. If a vacuum is applied, the pump membrane 84 flatly contacts the surface of the air side and the pump chamber 82 is filled with liquid. By alternately applying overpressure and vacuum in a corresponding sequence of the three successive pump chambers 82, a peristaltic movement of the liquid through all three pump chambers 82 and in the downstream fluidic system is caused.

The pump drive 16' is provided with three valves (not illustrated) which either pass overpressure or vacuum into the respective air channel 80. The valves, not illustrated in the Figs., thus represent the coupling between the pressurized air pump and the pump mechanism 36'.

Figure 3:
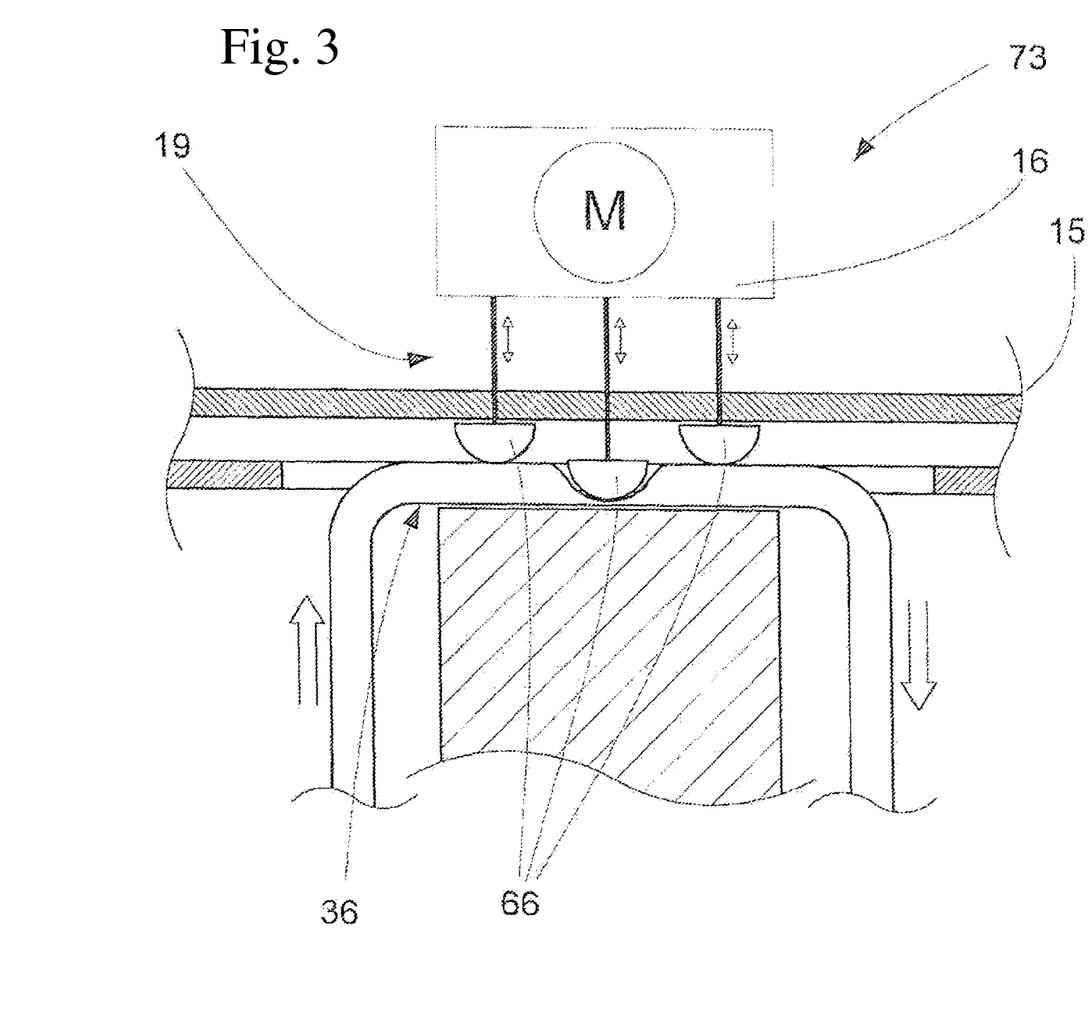
FIG. 3 shows an embodiment of a base-side electro-mechanical pump drive and a cartridge-side pump mechanism cooperating therewith.

As an alternative pump drive, the base module 14 comprises a drive motor 16, 17 with a coupling element 19 illustrated in FIG. 3. The coupling element 19 is formed by three peristaltic squeezing pistons 66 adapted to cause a peristaltic movement in a pump mechanism 36 designed as a flexible conduit section.

For the control of the analysis unit 10, the base module 14 further comprises a control 62.

The cartridge module 12 comprises three reservoir tanks 40, 41, 42 holding a carrier liquid, a reagent and waste liquid. The carrier liquid tank 40 and the reagent tank 41 are each connected to a peristaltic pump mechanism 36, 37 of their own via a liquid conduit, which pump mechanisms allow pumping the carrier liquid or the reagent in fine doses. The third reservoir tank 42 is a tank for waste liquid into which the waste liquid from the analytic sensor 20 flows.

The peristaltic pump mechanisms 36, 37 of the embodiment, together with the associated coupling elements 19, are designed such that an undesired return flow or leakage flow of carrier liquid or reagent cannot occur. On the cartridge module side, the peristaltic pump mechanisms 36, 37 are substantially formed by flexible sections of the respective liquid conduit driven by the respective coupling elements 19 of the associated drive motors 16, 17. The fluidic pump 72, 73 of the embodiment is thus formed by the drive motor 16, the coupling element 19 and the pump mechanism 36.

Further, the cartridge module 12 comprises an ion-selective dialysis membrane 26 through which analyte molecules and ions can migrate from the water 11 into the carrier liquid flowing by on the inside, while particles macromolecules and microorganisms are kept from passing the membrane. The carrier liquid thus enriched with the analyte molecules and ions forms the so-called sample. The dialysis membrane 26 has, for example, a pore size of less than 2 μm.

Finally, the cartridge module 12 includes the measuring section 60 of the fluidic system, which is formed by a straight conduit section 70 whose longitudinal ends have transparent light-permeable windows for the analyte sensor 20 to perform photometry.

When the cartridge module 12 is mounted to the base module 14, the measuring section 60 is exactly aligned with the base module-side parts of the analyte sensor 20. Further, the coupling elements 19 of the pumps 72, 73 are in peristaltic engagement with the pump mechanisms 36 on the cartridge module side.

In the analysis mode, the associated pump 72 pumps carrier liquid from the carrier liquid reservoir tank 40 to the dialysis membrane 26 through which analyte ions or molecules migrate from the water 11 into the carrier liquid. Thereafter, an associated pump 73 adds a reagent from the reagent reservoir tank 41 to the carrier liquid enriched in analyte ions, the so-called sample, whereby the analyte of interest in the carrier liquid is colored corresponding to its concentration. The colored sample is pumped to the measuring section 60 where it is photometrically analyzed by the analyte sensor 20, whereby the concentration of the analyte in the so-called sample can be determined, which in turn allows conclusions on the concentration of the analyte in the water around the analysis unit. The sample is therefore pumped into the waste reservoir tank 42.

Upon a depletion of the reagent or the carrier liquid in the corresponding reservoir tanks 40, 41, upon an imminent overflow of the waste reservoir tank 42, or upon a malfunction possible due to a component of the cartridge module 12, the cartridge module 12 is exchanged. In doing so, a lock (not illustrated) is unlocked and the cartridge module 12 is pulled off from the base module housing 15 in an axially downward direction. Here, the pump coupling element 19 is separated from the pump mechanism 36 and the measuring section 60 is removed from the analyte sensor 20. Subsequently, a new cartridge module 12 may be set to the housing 15, while the pump coupling elements 19 being connected to the pump mechanisms 36 again and the measuring section 60 is inserted into the analyzer 20.

Figure 4:
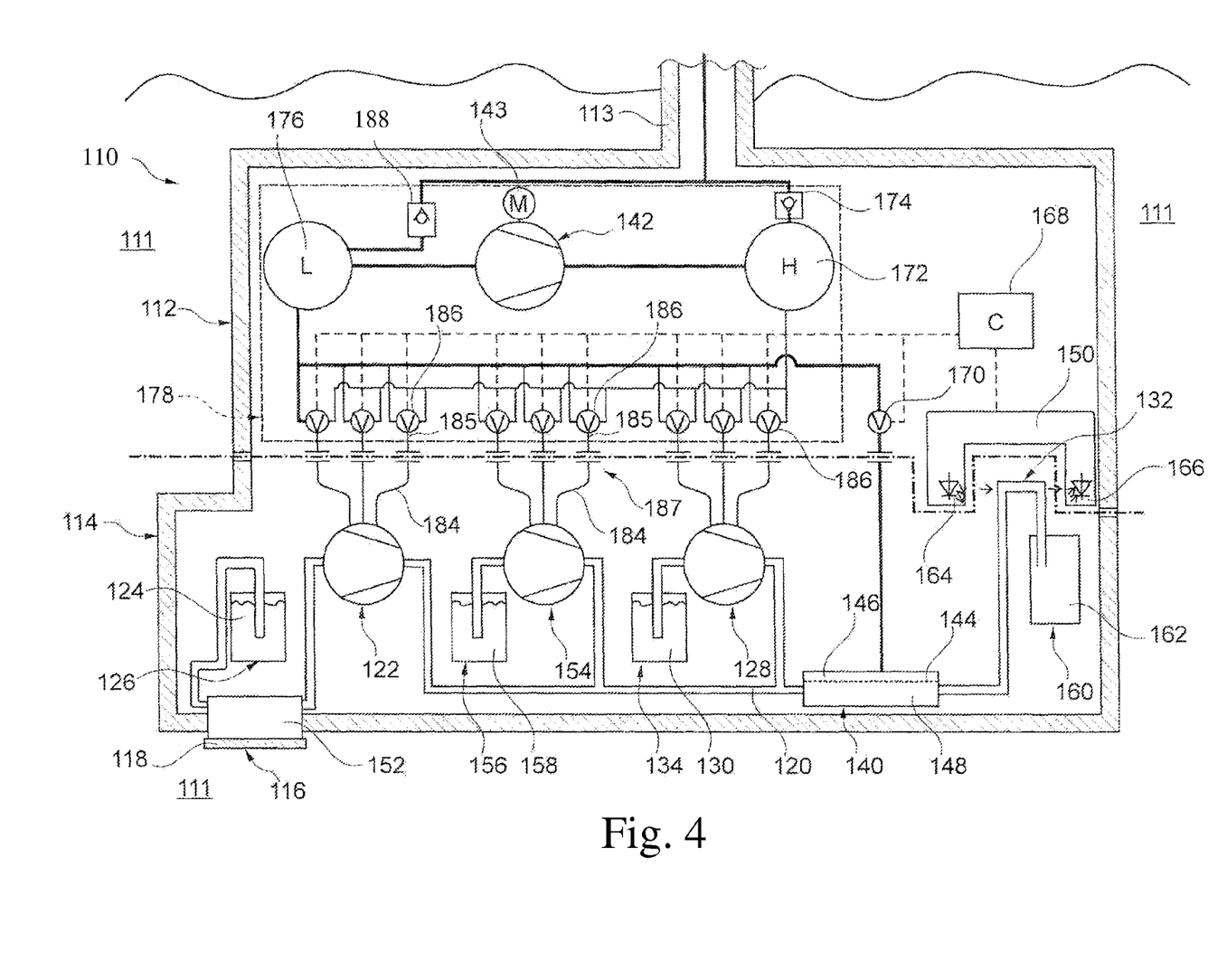
FIG. 4 shows a schematic illustration of an embodiment of a process analysis unit.

FIG. 4 is a schematic illustration of an embodiment of a process analysis unit 110 for a continuous or quasi-continuous quantitative photometric determination of an analyte, such as phosphate, ammonium or nitrate, in water. The analysis unit 110 is a stationary analysis unit 110 and is mounted immersed in the water 111 under analysis, i.e., it is configured as a so-called immersion probe. The analysis unit 110 consists of a base module 112 rigidly hung in or just above the water 111, i.e., the liquid under analysis, from a tubing 113, and an exchangeable cartridge module 114 removably fastened to the base module 112 and immersed in the water 111.

The entire fluidic system of the analysis unit 110 is provided in the cartridge module 114. The cartridge module 114 comprises a carrier liquid reservoir tank 126 holding a carrier liquid 124, which is connected to a sample taking device 116 via a conduit, the device being a dialysis device 116 in the present case. The dialysis device 116 comprises a dialysis membrane 118 as the membrane 118 which separates the dialysis chamber 152, in which the carrier liquid dwells during dialysis, from the water 111. The dialysis chamber 152 may be formed by a meandering groove, for example, whose groove opening is closed by the dialysis membrane 118. A first pump mechanism 122 is provided behind the dialysis device 116, which pumps the sample 120 or the dialysate from the dialysis device 116 to a degassing device 140.

The cartridge module 114 has a reagent reservoir tank 134 holding a liquid reagent 130 pumped to the degassing device 140 by a second pump mechanism 128. Further, the cartridge module 114 is provided with a standard solution reservoir tank 156 holding a standard solution 158, a third pump mechanism 154 being provided downstream of the standard solution reservoir tank 156, seen in the flow direction, which pumps the standard solution to the degassing device 140, if need be.

Figure 6:
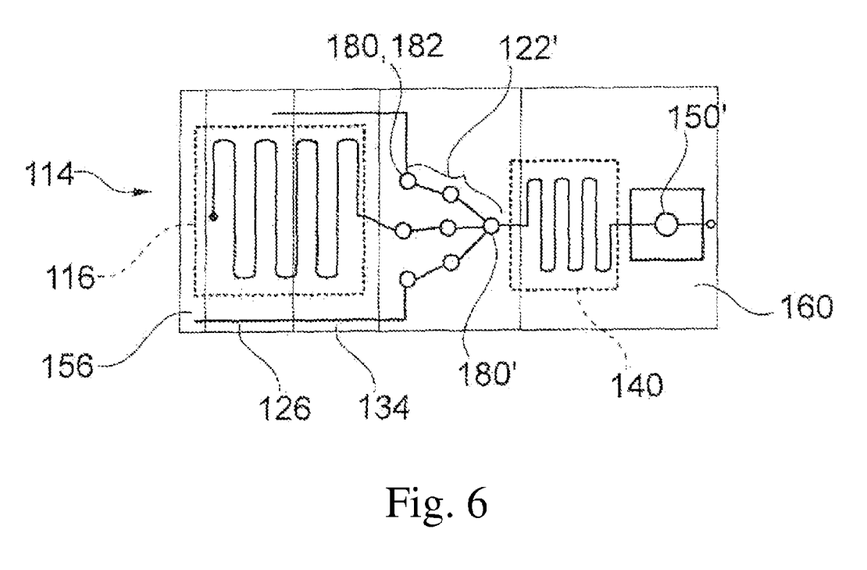
FIG. 6 shows a top plan view on the cartridge module of the analysis unit in FIG. 5.

The three pump mechanisms 122, 128, 154 converge in a star-shaped manner just before the degassing device 140, as is particularly well visible in FIG. 6. The degassing device 140 is formed by a groove-shaped degassing channel 148 covered by a gas-permeable and liquid-tight degassing membrane 144 which is a hydrophobic Teflon membrane. The degassing channel 148 extends in a meandering manner so that a relatively long degassing channel 148 is realized in a small area. On the side of the degassing membrane 144 opposite the degassing channel 148, the gas side 146 of the degassing device is arranged whose evacuation is controlled through a degassing valve 170 on the base module side.

The sample flows from the degassing device 140 to a photometer measuring section 132 and from there into a waste liquid tank 160 in which the waste liquid 162 is collected. The photometer measuring section 132 is functionally associated to a photometric analyte sensor 150 on the base module side which has a light source 164 and an optical detector 166 between which a section of the dialysate conduit is arranged in the longitudinal direction, which section forms the photometer measuring section. In the present case, the analyte sensor 150 is designed as a transmission photometer. Alternatively, the photometer may, however, also be designed as a reflection photometer 150', as illustrated in the embodiment in FIG. 5.

The pressure sources for driving the three pump mechanisms 122, 154, 128 are an overpressure accumulator 172 and a vacuum accumulator 176 in the base module 112. The three pump mechanisms 122, 154, 128 are designed as pneumatic peristaltic pumps. A respective valve bank is associated to each pump mechanism 122, 154, 128, each formed by three change-over valves 186. Each pump mechanism 121, 154, 128 respectively comprises three pump chambers 180 with a respective elastic pump membrane 182 made of rubber or an elastic plastic material.

The rear side of each pump membrane 182 is connected to a change-over valve 186 via a pneumatic control conduit 184 on the cartridge module side, a control conduit coupling 187 and a pneumatic control conduit 185 on the base module side, the change-over valve selectively connecting the pump membrane 182 with the overpressure accumulator 172 or the vacuum accumulator 176. In this manner, either an overpressure or a vacuum is applied to the rear side of the pump membrane 182 so that the pump chambers 180 are filled or emptied. By successively filling and emptying the three pump chambers 122, 154, 128, a peristaltic pumping movement is caused.

For the purpose of generating a vacuum in the vacuum accumulator 176 and an overpressure in the overpressure accumulator 172, a pneumatic pump 142 is provided in the base module 112, whose pump inlet is connected to the vacuum accumulator 176 and whose pump outlet is connected with the overpressure accumulator 172. The pneumatic pump 142 is driven continuously by an electric pneumatic pump motor 143. The vacuum in the vacuum accumulator 176 and the overpressure in the overpressure accumulator 172 are limited, respectively, by a corresponding vacuum valve 188 or an overpressure valve 174, each connected to atmospheric air pressure. As an alternative, the pressure sensors may be provided in the accumulators 172, 176, by means of which the pneumatic pump is activated or deactivated when pressure falls below a limit pressure or exceeds the same.

The entire pneumatic system which is basically formed by the valves 185, the pressure accumulators 172, 176, the pneumatic pump 142 and the motor 143, constitutes the respective independent pump drive 178 for the pump mechanisms 122, 154, 128.

The degassing valve 170 controlling the vacuum in the degassing device 140 is connected to the vacuum accumulator 176.

All valves 186, 170 and the photometer 150 are controlled by a central control 168. All electric components are arranged in the base module 112.

Figure 5:
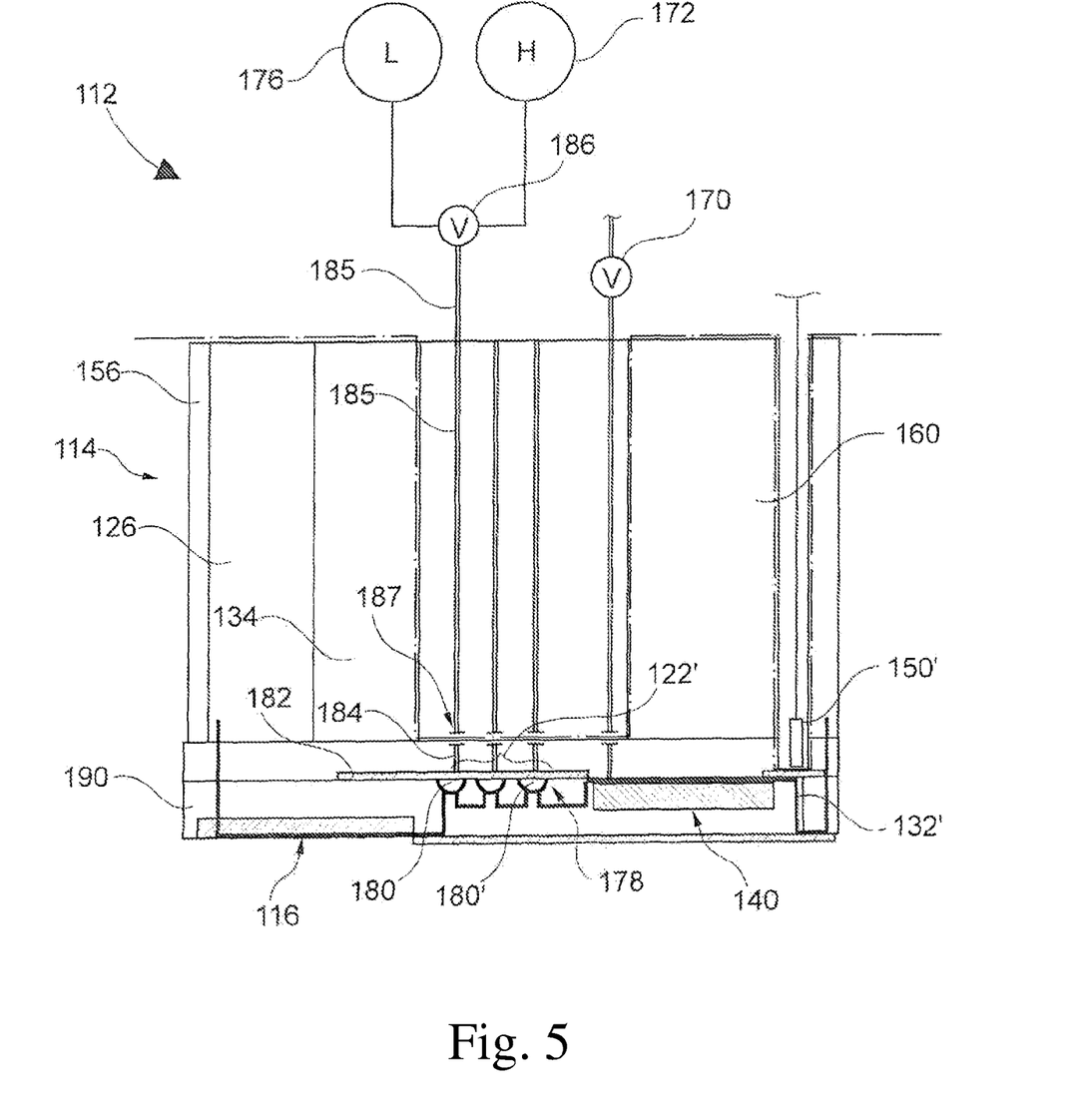
FIG. 5 shows a longitudinal section of an embodiment of an analysis unit.

FIGS. 5 and 6 illustrate an embodiment of an analysis unit or a cartridge module 114, respectively. A difference from the embodiment illustrated merely schematically in FIG. 4 is the concrete design of the three pump mechanisms 122', whose respective last pump chamber 180' is formed by a single common pump chamber 180'. Another difference of the embodiment in FIG. 5 is the design of the analyte sensor 150' as a reflection photometer.

As is clearly visible in FIGS. 5 and 6, the cartridge module 114 is substantially formed by a plate-shaped plastic part 190 comprising the fluidic system conduits, the pump chambers 180, 180', the dialysis module 116, the degassing device 140 as well as the measuring section 132', and by the tanks 126, 134, 156, 162 set on the plate-shaped plastic part 190.

The present invention is not limited to embodiments described herein; reference should be had to the appended claims.

What is claimed is:

1. A process analysis unit for the determination of an analyte in water, the process analysis unit comprising a base module and an exchangeable cartridge module which is configured to be connected to the base module,
the base module comprising:
at least one independent pump drive, and
an analyte sensor without a fluidic measuring section,
wherein the base module does not comprise a liquid fluidic system; and
the cartridge module comprising the liquid fluidic system, the cartridge module comprising:
a liquid reservoir tank,
a sample taking device,
at least one drive-less pump mechanism configured as a peristaltic membrane pump, the drive-less pump mechanism being configured to be driven pneumatically and to pump a liquid from the liquid reservoir tank, wherein the peristaltic membrane pump comprises pump chambers covered by a flexible liquid-tight pump membrane,
a fluidic measuring section for the analyte sensor, and
a plastic material plate with groove-like microfluidic channels configured to connect the liquid reservoir tank, the at least one drive-less pump mechanism, and a measuring section, a section of the groove-like microfluidic channels being less than 5 mm$^2$,
wherein,
when the cartridge module is connected to the base module, the at least one drive-less pump mechanism is connected to and is driven by the at least one independent pump drive, and the fluidic measuring section is connected to the analyte sensor, and
each of a plurality of the at least one drive-less pump mechanism is associated with a respective at least one independent pump drive.

2. The process analysis unit as recited in claim 1, wherein the cartridge module further comprises a plurality of reservoir tanks.

3. The process analysis unit as recited in claim 1, wherein the analyte sensor comprises an optical detector configured to optically determine the analyte in the fluidic measuring section.

4. The process analysis unit as recited in claim 3, wherein the optical detector determines at least one of an absorption, a fluorescence and a luminescence of a sample.

5. The process analysis unit as recited in claim 1, wherein the cartridge module further comprises a dialysis membrane configured to obtain a sample.

6. The process analysis unit as recited in claim 1, wherein the analysis unit is designed as an immersion probe.

7. The process analysis unit as recited in claim 1, wherein the cartridge module is configured to be encapsulated in a liquid-tight manner so that liquids contained therein cannot escape therefrom.

* * * * *